United States Patent [19]

Pfäffli

[11] 4,146,643

[45] Mar. 27, 1979

[54] INCREASING VIGILANCE OR TREATING CEREBRAL INSUFFICIENCY WITH SUBSTITUTED VINCAMINES

[75] Inventor: Paul Pfäffli, Arlesheim, Switzerland

[73] Assignee: Sandoz Ltd., Basel, Switzerland

[21] Appl. No.: 857,019

[22] Filed: Dec. 2, 1977

Related U.S. Application Data

[63] Continuation-in-part of Ser. No. 661,563, Feb. 26, 1976, abandoned, which is a continuation-in-part of Ser. No. 531,602, Dec. 11, 1974, abandoned.

[30] Foreign Application Priority Data

Dec. 18, 1973 [CH] Switzerland ..................... 17689/73
Feb. 6, 1974 [CH] Switzerland ..................... 1621/74
Feb. 8, 1974 [CH] Switzerland ..................... 1765/74

[51] Int. Cl.$^2$ .................. A61K 31/475; C07D 519/04
[52] U.S. Cl. ........................... 424/262; 260/326.13 B; 260/456 R; 546/51; 546/70; 546/201
[58] Field of Search ...................... 260/293.53, 293.55; 424/256, 262

[56] References Cited

U.S. PATENT DOCUMENTS 3,755,335   8/1973   Thal et al. ..................... 260/293.53

*Primary Examiner*—Natalie Trousof
*Assistant Examiner*—Richard A. Schwartz
*Attorney, Agent, or Firm*—Gerald D. Sharkin; Robert S. Honor; Thomas O. McGovern

[57] ABSTRACT

Halo-, hydroxy-, alkyl- and alkoxy-vincamine derivatives are useful vigilance increasing agents.

24 Claims, No Drawings

INCREASING VIGILANCE OR TREATING CEREBRAL INSUFFICIENCY WITH SUBSTITUTED VINCAMINES

This is a continuation-in-part of my copending application Ser. No. 661,563 of Feb. 26, 1976 now abandoned, which in turn is a continuation in part of my then copending application Ser. No. 531,602 of Dec. 11, 1974, which is now abandoned.

The present invention relates to new heterocylic compounds.

In accordance with the invention there are provided new compounds of formula I,

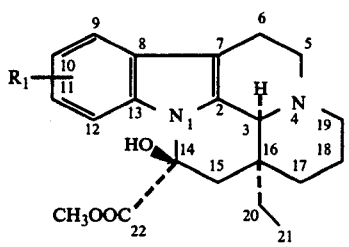

I wherein $R_1$ is bromine, fluorine, chlorine, hydroxyl, lower alkyl or lower alkoxy, with the proviso that when $R_1$ is in the 11 or 12 position this is other than methoxy.

Lower alkyl or alkoxy refers to 1 to 4 carbon atoms.

Further, in accordance with the invention a compound of formula I may be obtained by a process comprising (a) cyclizing a compound of formula II,

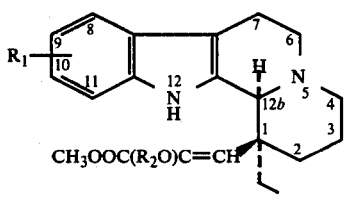

II wherein $R_1$ is bromine, fluorine, chlorine, hydroxyl, lower alkyl or lower alkoxy, and $R_2$ is lower alkyl, in the presence of acid, or (b) treating a compound of formula III,

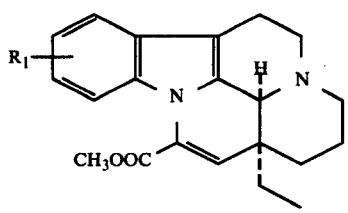

III wherein $R_1$ is as defined above, at a temperature below 0° C. with a hydrogen halide, and subsequently hydrolyzing the resulting reaction product, or (c) brominating vincamine to produce a compound of formula I',

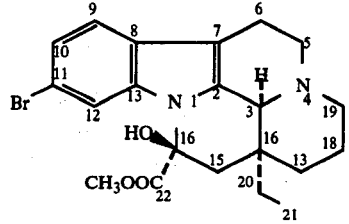

I'

Process variant (a) may, for example, be effected using a hydrogen halide solution, e.g. hydrochloric acid in methanol, aqueous hydrogen iodide or hydrogen bromide in glacial acetic acid. A temperature between 0° and 80° C., preferably a temperature between 10° and 60° C. may be used.

Reaction step (b) may be effected as follows: The compound of formula III may be allowed to react at a temperature below 0° C., preferably at a temperature from −150° C. to −20° C., with a preferably completely dry and preferably halogen-free hydrogen halide.

Hydrogen bromide is preferred as the hydrogen halide, although hydrogen chloride or hydrogen iodide may also be used.

The reaction solution may be subsequently evaporated to dryness, the residue may then be suspended, at a temperature below 0° C., preferably at a temperature from −150° C. to −20° C., in a suitable solvent which does not freeze at the reaction temperature, e.g. acetone or tetrahydrofuran. A suitable water-containing mixture which does not freeze at the reaction temperature, and comprising a solvent such as acetone or tetrahydrofuran, an organic or inorganic base, e.g. pyridine, sodium hydrogen carbonate or an alkali hydroxide, and water, preferably at a volume ratio of 70:20:10, may subsequently be added. The mixture is conveniently allowed to warm up to room temperature.

Process variant (c) may be effected in conventional manner for the introduction of bromine into the aromatic nucleus of such compounds. A catalyst such as iron (III) chloride or iron (III) bromide, boron tribromide, zinc (II) chloride, aluminium chloride or iodine may be used. The reaction may, for example, be effected by suspending optically active or racemic vincamine in an inert solvent, e.g. chloroform, chlorobenzene, methylene chloride.

Suitable temperatures are from −20° to +20° C. Bromine is preferably added in a solution of one of the above inert solvents to vincamine in a similar solution.

A compound of formula II used as starting material in process variant (a) may be obtained by reducing a compound of formula XI,

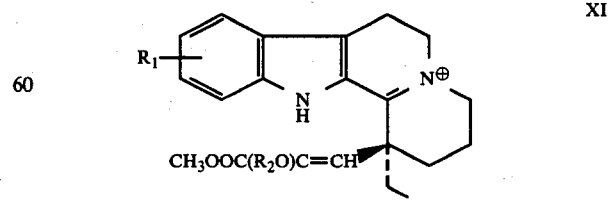

XI wherein $R_1$ is as defined above, and $R_2$ is lower alkyl.

The reduction may be effected either catalytically or in the presence of an organometallic compound. The catalytic reduction is preferably effected in an inert solvent, e.g. methanol or ethanol, with the addition of a weak base, e.g. potassium acetate or diethylamine. The reaction is preferably effected at room temperature and normal pressure. Of the usual hydrogenation catalysts the preferred ones are palladium catalysts, especially on carriers. When the hydrogen take up is complete, the reaction mixture is worked up, e.g. in such a manner that the catalyst is filtered off, the resulting enol ether of formula II, wherein $R_1$ and $R_2$ are as defined above, is isolated from the filtrate in known manner, purified and, if desired, any mixture of Z- and E-isomers is separated chromatographically.

The reduction may alternatively be effected with organometallic compounds, preferably lithium aluminium hydride. The reduction is preferably effected in an inert solvent, preferably cyclic or open chain ethers, e.g. tetrahydrofuran, dioxane, diethyl ether, diglyme or dibutyl ether. The reduction is preferably effected at a temperature between about 0° and 80° C. The decomposition of the reaction complex is subsequently effected in known manner, and the resulting enol ethers of formula II, wherein $R_1$ and $R_2$ are as defined above, are isolated from the reaction mixture and purified.

A compound of formula XI may be obtained by subjecting a compound of formula X,

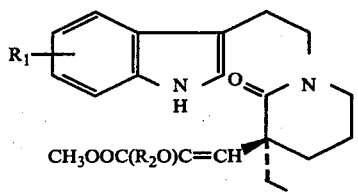

wherein
$R_1$ is as defined above, and
$R_2$ is lower alkyl,
to a Bischler-Napieralski ring closure.

The reaction may conveniently be effected by dissolving the compound of formula X in phosphorus oxychloride or polyphosphoric acid or a mixture of both, and boiling conveniently in an atmosphere of nitrogen or other inert gas.

Alternatively the ring closure may be effected by dissolving the compound of formula X in a mixture of phosphorus oxychloride and polyphosphoric acid and an inert solvent such as toluene, chlorobenzene or chloroform, and heating preferably at a temperature from 60° to 120° C.

The resulting immonium salt of formula XI may be isolated, from the reaction mixture in known manner. The salt of formula XI may be converted into the perchlorate salt form by precipitation with 10% aqueous sodium perchlorate from a methanolic solution, or by distribution of the immonium salt of formula XI between 10% sodium perchlorate/ethanol and methylene chloride.

A compound of formula X may be obtained by condensing a compound of formula IX,

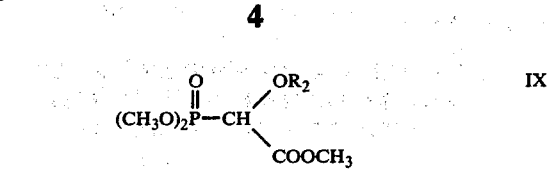

wherein $R_2$ is lower alkyl
with a compound of formula VIII,

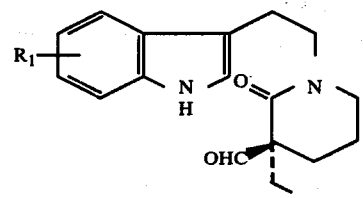

wherein $R_1$ is as defined above.

The reaction may, for example, be effected in a inert organic solvent, e.g. 1,2-dimethoxyethane, tetrahydrofuran, dioxane, diethyl ether or dimethyl formamide.

The reaction is preferably effected in the presence of a strongly basic condensation agent, e.g. an alkali metal amide such as sodium amide, an alkali metal hydride such as sodium hydride, or an alkali metal alcoholate such as potassium tert.butylate or sodium methylate. The reaction may conveniently be effected at room temperature.

The resulting mixture contains the Z and E isomer forms of the compound of formula X which may be isolated as such from the reaction mixture in known manner, e.g. chromatographically, or further separated into Z and E isomer forms in known manner.

The compound of formula VIII may be obtained by treating a compound of formula VII,

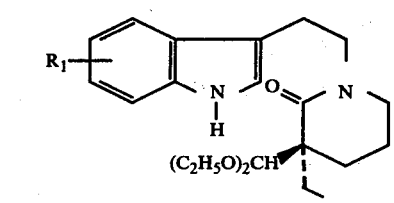

wherein $R_1$ is as defined above,
with acid, e.g. aqueous acetic acid, e.g. under reflux.

A compound of formula VII may be obtained by fusing a compound of formula VI,

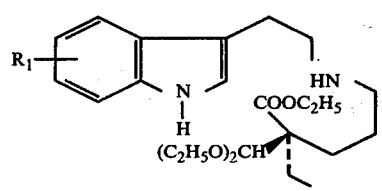

wherein $R_1$ is as defined above,
with imidazole.

A compound of formula VI may be produced by reacting (S)-ethyl-[3-(p-toluenesulphonyloxy)prop-1-yl]malonaldehydic acid ethyl ester diethyl acetal of formula IV

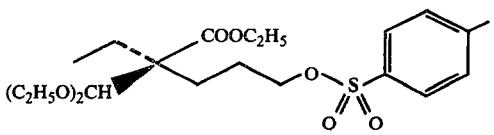

IV with a tryptamine derivative of formula V,

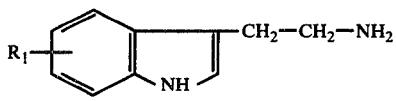

V wherein $R_1$ is as defined above.

Compounds of formula III used as starting materials in process variant (b) may be obtained from the reaction described in process variant (a).

A compound of formula I may be obtained in racemic form using racemic starting materials. Alternatively a compound of formula I may be obtained in individual optical isomer form, substantially free from its optical antipode, in conventional manner. For example diastereoisomeric salt fractional crystallization may be used, either of the compound of formula I or starting materials therefor.

Insofar as the preparation of any particular starting material is not particularly described, these compounds may be prepared in conventional manner, or by analogous processes to the processes described herein, or by analogous processes to known processes.

Similarly separation of isomers may be effected in conventional manner.

The free base forms of the compounds of formula I may be converted into acid addition salt forms in the usual manner and vice versa. A suitable acid is hydrobromic acid.

In the following non-limitative Examples all temperatures are indicated in degrees Centigrade and are uncorrected.

The optical rotation values refer to measurements with chloroform as solvent in all the optically active compounds.

EXAMPLE 1: (3S,14S,16S)-10-fluoro-vincamine and (3S,16S)-10-fluoro-apovincamine [process variant (a)]

10 cc of 33% hydrogen bromide in acetic acid are added to 3.86 g of a mixture of the Z and E isomers of 3-[(1S,12bS)-1-ethyl-9-fluoro-1,2,3,4,6,7,12,12b-octahydro-indolo[2,3-a]quinolizin-1-yl]-2-methoxy-propenoic acid methyl ester, and the mixture is stirred in an atmosphere of nitrogen for half an hour in a bath of 60°. Subsequent concentrating by evaporation yields a foam. This is dried at 50°/20 mm and pulverized. The residue is dissolved in 20 cc of methylene chloride, added dropwise to 20 cc of 2 N ammonia stirred at 0°, the water phase is separated, again extracted with 10 cc of methylene chloride, the 1st and then the 2nd organic phase are washed with 20 cc of the same wash water, are combined, dried with 3 g of sodium sulphate and concentrated by evaporation at 30°/20 mm. The resulting brown foam is chromatographed on 100 g of silica gel 0.05-0.20 mm, applied with methylene chloride/methanol (99:1) on a long thin column, in 100 cc fractions of the same solvent mixture. Fractions 8 to 13 contain the main quantity, fractions 14 to 30 smaller quantities of (3S,16S)-10-fluoro-apovincamine, crystallizable from methanol. The following fractions 31 to 36 are eluted with methylene chloride/methanol (98:2) and contain (3S,14S,16S)-10-fluoro-vincamine.

| (3S,14S,16S)-10-fluoro-vincamine: |  |
|---|---|
| M.P. 218° (dec.); $[\alpha]_D^{20} = -4,1°$ (1%, $CHCl_3$). | |
| NMR spectrum ($CDCl_3$, 100 megacycles per second): | |
| 0,89 | (T, 7 c.p.s./$H_3C(21)$/3 H) |
| 1,17 – 3,44 | (M /14 H) |
| among them at 2,10 + 2,20 (AB,15 c.p.s./$H_2C(15)$) | |
| 3,80 | (S /$H_3COOC(22)$/3 H) |
| 3,88 | (S /HC(3) /1 H) |
| 4,62 | (S /HOC(14) /1 H /exchangeable) |
| 6,66–7,20 | (M /HC(9,11,12)/3 H) |
| (3S,16S)-10-fluoro-apovincamine: | |
| M.P. 174°; $[\alpha]_D^{20} = +155°$ (1%, $CHCl_3$). | |
| NMR spectrum ($CDCl_3$, 100 megacycles per second): | |
| 1,01 | (T,7 c.p.s./$H_3C(21)$/ 3 H) |
| 1,22–3,53 | (M / 12 H) |
| among them at 1,91 (Q,7 c.p.s./$H_2C(20)$) | |
| 3,93 | (S /$H_3COOC(22)$/3 H) |
| 4,11 | (S /HC(3) /1 H) |
| 6,14 | (S /HC(15) /1 H) |
| 6,70–7,27 | (M /HC(9,11,12)/3 H) |

The 3-[(1S,12bS)-1-ethyl-9-fluoro-1,2,3,4,6,7,12,12b-octahydro-indolo[2,3-a]quinolizin-1-yl]-2-methoxy-propenoic acid methyl ester, used as starting material, is produced as follows:

(a)
(S)-3-ethyl-3-diethoxymethyl-1-[2-(5-fluoro-indol-3-yl)-ethyl]-2-piperidone

100 Millimols of crude (S)-ethyl-[3-(p-toluenesulphonyloxy)-prop-1-yl]-malonaldehydic acid ethyl ester diethylacetal are dissolved in 50 cc of dimethyl sulphoxide at a bath temperature of 30°, a solution of 17.82 g of 5-fluoro-tryptamine in 50 cc of dimethyl sulphoxide is slowly added while stirring, and stirring is effected at 30° for 16 hours. 200 cc of a 2 N sodium carbonate solution and 100 cc of toluene are subsequently added dropwise at 23° while stirring. The resulting mixture is filtered and washed with 50 cc of toluene. The water phase of the filtrate is separated, extraction is effected with 50 cc of toluene and both toluene phases are successively washed with 200 cc of the same mixture water/ethanol (80:20). The combined toluene phases are stirred with 20 g of sodium sulphate, filtration and evaporation at 40°/20 mm are effected, whereby crude (S)-2-ethyl-2-diethoxymethyl-5-[2-(5-fluoro-indol-3-yl)ethylamino]-pentanoic acid ethyl ester results as yellow, clear oil. The so obtained product may be used without further purification for the reaction with imidazole.

This crude material is mixed with 100 g of imidazole. The mixture is melted at 100° and left at 130° in an atmosphere of nitrogen for 20 hours. After cooling the reaction solution to 100°, the melted material is poured into 80 cc of toluene having a temperature of 100°. The solution which is cooled while stirring begins to form crystals at 45°, and at 0° is a mash which can still be stirred. 300 cc of 6 N hydrochloric acid are added dropwise to this mash at 0° with stirring and strong cooling. The water phase is separated in the cold, extraction is effected with 50 cc of toluene, and both toluene phases are washed with 100 cc of the same aqueous 2 N ammonia solution. After concentrating the combined toluene phases by evaporation at 40°/20 mm, a yellowish oil is obtained, which is chromatographed on 50 parts of silica gel with methylene chloride/methanol (98:2) in fractions of 25 parts. The combined residues of fractions 8 to 10 yield white crystals after crystallization from ethyl acetate/hexane (20:80) at 0°, M.P. 101°; $[\alpha]_D^{20} = +6.7°$ (1%, CHCl$_3$), of the title compound (a).

(b)
(S)-3-ethyl-3-formyl-1-[2-(5-fluoro-indol-3-yl)-ethyl]-2-piperidone 39.05 g of (S)-3-ethyl-3-diethoxymethyl-1-[2-(5-fluoro-indol-3-yl)-ethyl]-2-piperidone are mixed with 80 cc of 99% acetic acid and 20 cc of water. The mixture is heated to the boil for half an hour in an atmosphere of nitrogen. After cooling, the solvent is removed by evaporation; the oily residue is subsequently taken up twice in 50 cc amounts of toluene and again concentrated by evaporation in order to remove most of the water and acetic acid. After crystallization from ethyl acetate/hexane (1:2) at 0°, brownish crystals are obtained. M.P. 116°, $[\alpha]_D^{20} = -31.5°$ (1%, CHCl$_3$).

(c)
3-{(S)-3-ethyl-1-[2-(5-fluoro-indol-3-yl)-ethyl]-2-oxo-3-piperidyl}-2-methoxy-propenoic acid methyl ester 3.185 g of dimethylphosphonomethoxyacetic acid methyl ester are added dropwise at room temperature to a suspension of 360 mg of sodium hydride in 10 cc of absolute tetrahydrofuran in the absence of moisture. After stirring at room temperature for 30 minutes, a solution of 3.164 g of (S)-3-ethyl-3-formyl-N-[2-(5-fluoro-indol-3-yl)-ethyl]-2-piperidone in 10 cc of absolute tetrahydrofuran is added dropwise to the reaction solution. The reaction mixture is subsequently stirred at room temperature for a further 2 hours, is poured on ice and extracted with methylene chloride. The organic phases are dried and concentration is effected. A yellowish oil is obtained, consisting of a mixture of the Z and E isomers of 3-{(S)-3-ethyl-1-[2-(5-fluoroindol-3-yl)-ethyl]-2-oxo-3-piperidyl}-2-methoxy-propenoic acid methyl ester.

(d)
(S)-1-ethyl-9-fluoro-1-(2-methoxy-2-methoxycarbonyl-vinyl)-2,3,4,5,7,12-hexahydro-1H-indolo[2,3-a]quinolizin-5-ium perchlorate 4.025 g of a mixture of E/Z isomers of 3-{(S)-3-ethyl-1-[2-(5-fluoro-indol-3-yl)-ethyl]-2-oxo-3-piperidyl}-2-methoxy-propenoic acid methyl ester are dissolved in 5 cc of phosphorus oxychloride, and the solution is boiled in an atmosphere of nitrogen for 3 hours. The solution is subsequently evaporated at 60° and 20 mm, and subsequently at 60° for 15 minutes in a high vacuum. After taking up in 10 cc of chloroform, evaporation is repeated in analogous manner, whereby the crude iminium chloride is obtained as yellow-brown foam. 20 g of silica gel 0.05–0.20 mm are applied on a column with methylene chloride, the crude iminium chloride is dissolved in methylene chloride at 30° and placed on the column. Washing is then effected with methylene chloride until shortly before the appearance of the clearly visible, dark brown zone on the column outlet (100–200 cc). Elution is subsequently effected with 120 cc of methylene chloride/methanol (90:10) and this eluate is concentrated by evaporation at 30°/20 mm until a foam is obtained.

50 cc of 10% sodium perchlorate are added to water at 0°, and the solution of the above foam in 5 cc of methanol is added dropwise while stirring. The light yellow precipitate is filtered at 0°, is washed twice with 20 cc amounts of water and suction-dried. Water is removed by distillation from the residue at 20 mm and a bath temperature of 30° until a solution results. This is added dropwise at 0° to 50 cc of sodium perchlorate (10%), the precipitate is filtered in the cold, is washed 6 times with 20 cc amounts of water having a temperature of 0° and is suction-dried. Drying is subsequently effected, whereby the title compound is obtained in the form of an E and Z isomer mixture.

(e)
3-[(1S,12bS)-1-ethyl-9-fluoro-1,2,3,4,6,7,12,12b-octahydro-indolo[2,3-a]quinolizin-1-yl]-2-methoxypropenoic acid methyl ester The E and Z isomer mixture of (S)-1-ethyl-9-fluoro-1-(2-methoxy-2-methoxycarbonylvinyl)-2,3,4,6,7,12-hexahydro-1H-indolo[2,3-a]quinolizin-5-ium perchlorate is dissolved at 30° in 10 cc of methylene chloride/ethanol (80:20), and the solution is added to a prehydrogenated mixture of 982 mg of potassium acetate, 2 g of 10% Pd on charcoal and 8 cc of ethanol, as well as 2 cc of water. The mixture is then hydrogenated at room temperature and normal pressure, while stirring, until 8 millimols of hydrogen have been taken up and hydrogen consumption practically stops. After filtering through Hyflo, and washing with 20 cc of methylene chloride/ethanol (80:20), the filtrate is concentrated by evaporation at 30°/20 mm, the residue is dissolved in 20 cc of methylene chloride, mixed at 0° with 20 cc of 2 N ammonia and divided. The organic phase is separated, extracted with 10 cc of methylene chloride, the 1st and 2nd methylene chloride phases are washed with 20 cc of the same water, combined and dried with sodium sulphate. The reaction mixture is concentrated by evaporation at 30°/20 mm, pulverized, and dried in a high vacuum, whereby a mixture of the Z and E isomers of 3-[(1S,12bS)-1-ethyl-9-fluoro-1,2,3,4,6,7,12,12b-octahydro-indolo[2,3-a]quinolizin-1-yl]-2-methoxy-propenoic acid methyl ester is obtained in crude form as yellow-brown residue.

EXAMPLE 2:
(3S,14S,16S)-10-fluoro-vincamine[process variant b)]

1 cc of absolutely dry and bromine-free hydrogen bromide is condensed with 354.4 mg of (3S,16S)-10-fluoro-apovincamine at −78°. After stirring at −78° for 15 minutes the resulting solution is evaporated to dryness at −78° and a pressure of 20 mm, the reaction vessel is filled with dry nitrogen, and evacuation and filling with nitrogen are repeated twice.

The residue is first suspended at −78° in 5 cc of acetone having a temperature of −78°, 1.5 cc of 10 N potassium hydroxide are subsequently added at −40° while stirring vigorously, the resulting mash is stirred at −40° for 1 hour and is neutralized with 1 g of solid carbon dioxide while stirring. The reaction mixture is subsequently divided between 20 cc of methylene chloride and 7 cc of 2 N ammonia, the aqueous phase is extracted with 10 cc of methylene chloride and both methylene chloride phases are successively washed with 5 cc of the same wash water, dried with sodium sulphate and concentrated by evaporation.

The residue is (3S,14S,16S)-10-fluoro-vincamine with small amounts of (3S,16S)-10-fluoro-apovincamine and (3S,14R,16S)-10-flouro-14-epivincamine as by-products. Crystallization from toluene yields (3S,14S,16S)-10-fluoro-vincamine, having the characteristics indicated in Example 1.

(3R,14R,16R)-10-fluoro-vincamine, having the same characteristics as (3S,14S,16S)-10-fluoro-vincamine, but an inverse direction of rotation, is obtained in analogous manner, using (3R,16R)-10-fluoro-apovincamine as starting material.

Racemic 10-fluoro-vincamine is obtained in analogous manner, using racemic 10-fluoro-apovincamine as starting material; M.P. 230° (decomp.).

EXAMPLE 3

(3S,16S)-10-methoxy-apovincamine, (3S,16S)-10-hydroxy-apovincamine, (3S,14S,16S)-10-methoxy-vincamine, and (3S,14S,16S)-10-hydroxy-vincamine[process variant a)]

10 cc of 33% hydrogen bromide in acetic acid are added to 3.985 g of a mixture of the Z and E isomers of 3-[(1S,12bS)-1-ethyl-9-methoxy-1,2,3,4,6,7,12,12b-octahydro-indolo[2,3-a]quinolizin-1-yl]-2-methoxypropenoic acid methyl ester, and stirring is effected in an atmosphere of nitrogen for half an hour in a bath of 60°. Subsequent concentrating by evaporation gives a foam. This is dried at 50°/20 mm and pulverized. The residue is dissolved in 20 cc of methylene chloride, is added dropwise to 20 cc of 2 N ammonia stirred at 0°, the water phase is separated, extracted with 10 cc of methylene chloride, the 1st and then the 2nd organic phase are washed with 20 cc of the same wash water, are combined, dried with 3 g of sodium sulphate and concentrated by evaporation at 30°/20 mm. The resulting brown foam is chromatographed on 100 g of silica gel 0.05–0.20 mm, applied with methylene chloride/methanol (96:4) on a long, thin column, in 100 cc fractions with methylene chloride containing 4–10% of methanol.

The products are eluted in the following sequence: with methylene chloride/methanol (96:4) (3S,16S)-10-methoxy-apovincamine, then (3S,14S,16S)-10-methoxy-vincamine; with methylene chloride/methanol (90:10) (3S,16S)-10-hydroxy-apovincamine, then (3S,14S,16S)-10-hydroxy-vincamine. (3S,16S)-10-methoxy-apovincamine may be crystallized as hydrobromide from isopropyl alcohol, (3S,16S)-10-hydroxy-apovincamine as base from toluene.

(3S,16S)-10-methoxy-apovincamine
M.P. (hydrobromide) = 235° (dec.); $[\alpha]_D^{20}$ (base) = + 109° (0,25%, CHCl$_3$).
NMR spectrum (CDCl$_3$, 100 megacycles per second):

| | |
|---|---|
| 1,02 | (T, 7c.p.s./H$_3$C(21) / 3 H) |
| 1,20–3,44 | (M / 12 H) |
| | among them at 1,92 (Q, 7 c.p.s./ H) |
| 3,85 | (S / H$_3$C—O—C(10) / 3 H) |
| 3,93 | (S / H$_3$COOC(22) /3 H ) |
| 4,13 | (S / HC(3) / 1 H) |
| 6,10 | (S / HC(15) / 1 H) |
| 6,78 | (Q, 9 + 3 c.p.s./HC(11) 1 H ) |
| 6,91 | (D, 3c.p.s./HC(9) /1 H) |
| 7,13 | (D, 9c.p.s./HC(12) / 1 H) |

(3S,16S)-10-hydroxy-apovincamine:
M.P. = 226° (dec.); $[\alpha]_D^{20}$ = + 121° (0,25%, CHCl$_3$).
NMR spectrum (CDCl$_3$, 100 megacycles per second):

| | |
|---|---|
| 1,00 | (T, 7c.p.s./H$_3$C(21) / 3 H) |
| 1,23–3,51 | (M /12 H) |
| | among them at 1,92 (Q, 7c.p.s./H$_2$C(20) ) |
| 3,92 | (S / H$_3$COOC(22) / 3 H) |
| 4,16 | (S / HC(3) / 1 H) |
| ap. 6 | (br. S / HO—C(10), exchangeable / 1 H) |
| 6,07 | (S / HC(15) / 1 H) |
| 6,68 | ( Q, 9 + 2c.p.s./HC(11) / 1 H) |
| 6,83 | (D, 2c.p.s./HC(9) / 1 H) |
| 7,07 | (D, 9c.p.s./HC(12) / 1 H) |

(3S,14S,16S)-10-methoxy-vincamine
M.P. 160° ;$[\alpha]_D^{20}$ = + 16,2° (0,3%, CHCl$_3$).
NMR spectrum (CDCl$_3$, 100 megacycles per second):

| | |
|---|---|
| 0,90 | (T, 7c.p.s./H$_3$C(21) / 3 H) |
| 1,12–3,43 | (M /14 H) |
| | among them at 2,09 + 2,20 (AB, 14c.p.s./H$_2$C(15) ) |
| 3,80 + 3,82 | 2 S / H$_3$C—O—C(10) + H$_3$COO(22) / 6 H) |
| 3,88 | (S / HC(3) / 1 H) |
| 4,60 | (S /HO—C(14), exchangeable / 1 H) |
| 6,72 | (Q, 9 + 3c.p.s./HC(11) / 1 H) |
| 6,86–7,20 | (M / HC(9) + HC(12) / 2 H) |

(3S,14S,16S)-10-hydroxy-vincamine
M.P. (hydrogen fumarate) = 207° (dec.);
$[\alpha]_D^{20}$ (base) = + 25,1° (0,25%, CHCl$_3$).
NMR spectrum (CDCl$_3$, 100 megacycles per second):

| | |
|---|---|
| 0,89 | (T, 7 c.p.s./H$_3$C(21) / 3 H) |
| 1,14–3,51 | (M /14 H) |
| | among them at 2,11 + 2,21 (AB,14c.p.s./H$_2$C(15) ) |
| 3,82 | (S /H$_3$COOC(22) / 3 H) |
| 3,93 | (S /HC(3) / 1 H) |
| ap. 4,7 | (br. S /HO—C(10) + HO—C(14); exchangeable / 2 H) |
| 6,64 | (Q, 9 + 3c.p.s./HC(11) / 1 H) |
| 6,77–7,03 | (M / HC(9) + HC(12) / 2 H) |

The 3-[(1S,12bS)-1-ethyl-9-methoxy-1,2,3,4,6,7,12,12b-octahydro-indolo[2,3-a]quinolizin-1-yl]-2-methoxypropenoic acid methyl ester, used as starting material, is produced as follows:

(a) (S)-3-ethyl-3-formyl-1-[2-(5-methoxy-indol-3-yl)-ethyl]-2-piperidone 100 millimols of crude (S)-ethyl-[3-(p-toluylsulphonyloxy)-prop-1-yl]-malonaldehydic acid ethyl ester diethyl acetal are dissolved in 50 cc of dimethylsulphoxide at a bath temperature of 30°, a solution of 19.02 g of 5-methoxy-tryptamine in 50 cc of dimethylsulphoxide is slowly added while stirring, and stirring is effected at 30° for 16 hours. 200 cc of a 2 N sodium carbonate solution and 100 cc of toluene are subsequently added dropwise at 23° while styrring. The resulting mixture is filtered and washed with 50 cc of toluene. The water phase of the filtrate is separated, extraction is effected with 50 cc of toluene, and both toluene phases are successively washed with 200 cc of the same mixture water/ethanol (80:20). The combined toluene phases are stirred with 20 g of sodium sulphate, filtered and concentrated by evaporation at 40°/20 mm, whereby crude (S)-2-ethyl-2-diethoxymethyl-5-[2-(5-methoxy-indol-3-yl)-ethylamino]-pentanoic acid ethyl ester is obtained as brown oil. The so obtained product may be used without further purification for the reaction in imidazol.

This crude material is mixed with 100 g of imidazol. The mixture is melted at 100° and left at 130° for 20 hours in an atmosphere of nitrogen. After cooling the reaction solution to 100°, the melted material is poured into 80 cc of toluene having a temperature of 100°. The solution cooled with stirring begins to form crystals at 45°, and at 0° is a mash which can still be stirred. 300 cc of 6 N hydrochloric acid are added dropwise at 0° to this mash while stirring. The water phase is separated in the cold, extraction is effected with 50 cc of toluene, and both toluene phases are washed with 100 cc of the same aqueous 2 N ammonia solution. The combined toluene phases yield a brown oil [diethoxyacetal of the title compound a)] after concentrating at 40°/20 mm. This oil is mixed with 80 cc of 99% acetic acid and 20 cc of water. The mixture is heated to the boil for half an hour in an atmosphere of nitrogen. After cooling the solvent is evaporated; the oily residue is subsequently taken up twice in 50 cc amounts of toluene and again concentrated by evaporation, in order to remove most of the water and acetic acid.

A rough chromatography on 10 parts of silica gel 0.05–0.20 mm with methylene chloride:methanol = 98:2 in fractions, corresponding to 5 parts, yields in fractions 5–12 a yellow oil, which may be crystallized from ethyl acetate:hexane = 3:7 at 0°. White crystals of (S)-3-ethyl-3-formyl-1-[2-(5-methoxy-indol-3-yl)-ethyl]-2-piperidone are obtained. M.P. 108°; $[\alpha]_D^{20} = -24.3°$ (1%, CHCl$_3$).

(b)
3-{(S)-3-ethyl-1-[2-(5-methoxy-indol-3-yl)-ethyl]-2-oxo-3-piperidyl}-2-methoxy-propenoic acid methyl ester 3.185 g of dimethylphosphonomethoxyacetic acid methyl ester are added dropwise at room temperature to a suspension of 360 mg of sodium hydride in 10 cc of absolute tetrahydrofuran in the absence of moisture. After stirring at room temperature for 30 minutes, a solution of 3.284 g of (S)-3-ethyl-3-formyl-N-[2-(5-methoxy-indol-3-yl)-ethyl]-2-piperidone in 10 cc of absolute tetrahydrofuran is added dropwise at room temperature to the reaction solution while stirring for 30 minutes. The reaction mixture is subsequently stirred at room temperature for a further 2 hours, poured on ice and extracted with methylene chloride. The organic phases are dried and concentrated. A yellowish oil, consisting of a mixture of the Z and E isomers of 3-{(S)-3-ethyl-1-[2-(5-methoxy-indol-3-yl)ethyl]-2-oxo-3-piperidyl}-2-methoxy-propenoic acid methyl ester, is obtained.

(c)
(S)-1-ethyl-9-methoxy-1-(2-methoxy-2-methoxycarbonylvinyl)-2,3,4,6,7,12-hexahydro-1H-indolo[2,3-a]quinolizin-5-ium perchlorate 4.145 g of a mixture of the Z and E isomers of 3-{(S)-3-ethyl-1-[2-(5-methoxy-indol-3-yl)-ethyl]-2-oxo-3-piperidyl}-2-methoxy-propenoic acid methyl ester are treated in a manner analogous to that described in Example 1 (d), whereby a mixture of isomers of the above title compound is obtained.

(d)
3-[(1S,12bS)-1-ethyl-9-methoxy-1,2,3,4,6,7,12,12b-octahydro-indolo[2,3-a]quinolizin-1-yl]-2-methoxy-propenoic acid methyl ester The E and Z isomer mixture of (S)-1-ethyl-9-methoxy-1-(2-methoxy-2-methoxycarbonylvinyl)-2,3,4,6,7,12-hexahydro-1H-indolo[2,3-a]quinolizin-5-ium perchlorate is treated in a manner analogous to that described in Example 1 (e), whereby a mixture of the Z and E isomers of 3-[(1S,12bS)-1-ethyl-9-methoxy-1,2,3,4,7,12,12b-octahydro-indolo[2,3-a]quinolizin-1-yl]-2-methoxy-propenoic acid methyl ester is obtained.

EXAMPLE 4:
(3S,14S,16S)-10-methoxy-vincamine[process variant b)]

1 cc of absolutely dry and bromine-free hydrogen bromide is condensed with 447.4 mg of (3S,16S)-10-methoxy-apovincamine hydrobromide at −78°. After stirring at −78° for 15 minutes, the resulting solution is evaporated to dryness at −78° and a pressure of 20 mm, the reaction vessel is filled with dry nitrogen, and evacuation and filling with nitrogen are repeated twice.

The residue is first suspended at −78° in 5 cc of acetone having a temperature of −78°, 1.5 cc of 10 N potassium hydroxide are subsequently added at −40° while stirring vigorously, the resulting mash is stirred at −40° for 1 hour and is neutralized with 1 g of solid carbon dioxide while stirring. The reaction mixture is subsequently divided between 20 cc of methylene chloride and 7 cc of 2 N ammonia, the water phase is extracted with 10 cc of methylene chloride, and both methylene chloride phases are successively washed with 5 cc of the same wash water, are dried with sodium sulphate and concentrated by evaporation.

The residue is (3S,14S,16S)-10-methoxy-vincamine with small amounts of (3S,16S)-10-methoxy-apovincamine and (3S,14R,16S)-10-methoxy-14-epivincamine as by-products. Crystallization from isopropyl alcohol yields (3S,14S,16S)-10-methoxy-vincamine with the same data as indicated in Example 3.

(3R,14R,16R)-10-methoxy-vincamine, having the same characteristics as (3S,14S,16S)-10-methoxy-vincamine, but an inverse direction of rotation, is obtained in analogous manner, using (3R,16R)-10-methoxy-apovincamine as starting material.

Racemic 10-methoxy-vincamine is obtained in analogous manner, using racemic 10-methoxy-apovincamine as starting material; M.P. 230° (decomp.).

EXAMPLE 5:
(3S,14S,16S)-10-hydroxy-vincamine[process variant b)]

1 cc of absolutely dry and bromine-free hydrogen bromide is condensed with 357.4 mg of (3S,16S)-10-hydroxy-apovincamine at −78°. After stirring at −78° for 15 minutes, the resulting solution is evaporated to dryness at −78° and a pressure of 20 mm, the reaction vessel is filled with dry nitrogen, and evacuation and filling with nitrogen are repeated twice.

The residue is first suspended at −78° in 5 cc of acetone having a temperature of −78°, 1.5 cc of 10 N potassium hydroxide are subsequently added at −40° while stirring vigorously, the resulting mash is stirred at −40° for 1 hour and is neutralized with 1 g of solid carbon dioxide while stirring. The reaction mixture is subsequently divided between 20 cc of methylene chloride and 7 cc of 2 N ammonia, the water phase is extracted with 10 cc of methylene chloride, and both methylene chloride phases are successively washed with 5 cc of the same wash water, dried with sodium sulphate and concentrated by evaporation.

The residue is (3S,14S,16S)-10-hydroxy-vincamine with small amounts of (3S,16S)-10-hydroxy-apovincamine and (3S,14R,16S)-10-hydroxy-14-epivincamine as by-products. Crystallization from isopropyl alcohol in the presence of fumaric acid yields crystals of (3S,14S,16S)-10-hydroxy-vincamine hydrogen fumarate . isopropyl alcohol having the data indicated in Example 3.

(3R,14R,16R)-10-hydroxy-vincamine, having the same characteristics as (3S,14S,16S)-10-hydroxy-vincamine, but an inverse direction of rotation, is obtained in analogous manner, using (3R,16R)-10-hydroxy-apovincamine as starting material.

Racemic 10-hydroxy-vincamine is obtained in analogous manner, using racemic 10-hydroxy-apovincamine as starting material; M.P. 230° (decomp.).

EXAMPLE 6:
(3S,14S,16S)-11-bromo-vincamine[process variant c)]

14.19 g of (3S,14S,16S)-vincamine and 10.81 g of iron trichloride hexahydrate are suspended at 0° in 80 cc of chloroform, and 44 cc of a 1 molar solution of bromine in chloroform are added dropwise thereto while stirring. After further stirring at 0° for half an hour 120 cc of 2 N ammonia are added, the rusty brown precipitate is filtered off, the two phases of the filtrate are separated, the water phase is extracted with 40 cc of methylene chloride, the organic phases are washed with water, combined, dried with sodium sulphate and concentrated by evaporation.

The residue is taken up in 80 cc of isopropyl alcohol, whereby spontaneous crystallization occurs. These crude crystals of (3S,14S,16S)-11-bromo-vincamine are isolated at 0°.

Pure (3S,14S,16S)-11-bromo-vincamine is obtained by chromatography of the crude crystals on silica gel with methylene chloride:methanol = 98:2 as solvent, and subsequent crystallization from isopropyl alcohol.

M.P. 214° (dec.); $[\alpha]_D^{20} = +8.7°$ (1%, CHCl$_3$).

| NMR spectrum (CDCl$_3$, 100 megacycles per second): | |
|---|---|
| 0,86 | (T, 7c.p.s./ H$_3$C(21) / 3 H) |
| 1,18–3,49 | (M / 14 H) |
| among them at ap.2,07 + 2,16 (AB, 15c.p.s./H$_2$C(15) | |
| 3,80 | (ap. S / H$_3$COOC(22) + HC(3) / 4 H) |
| 4,63 | (S / HO—C(14), exchangeable / 1 H) |
| 7,04–7,48 | (M / HC(9 + 10 + 12) / 3 H) |

(3S,14S,16S)-11-bromovincamine hydrogen fumarate is produced in conventional manner from the free base form. M.Pt. 144°; $[\alpha]_D^{20} = +4.7°$ (0.388% in H$_2$O)

Racemic 11-bromo-vincamine is obtained in analogous manner, using racemic vincamine as starting material; M.P. 230° (decomp.).

EXAMPLE 7: (3S,14S,16S)-9-fluoro-vincamine [process variant b)]

1 cc of absolutely dry and bromine-free hydrogen bromide is condensed with 354.4 mg of (3S,16S)-9-fluoro-apovincamine at −78°. After stirring at −78° for 15 minutes, the resulting solution is evaporated to dryness at −78° and 20 mm and is dried for 16 hours under these conditions.

The residue is first suspended at −78° in 5 cc of acetone having a temperature of −78°, 1.5 cc of 10 N aqueous potassium hydroxide are then added at −40° while stirring vigorously, the resulting mash is further stirred at −40° for 1 hour, is neutralized with 1 g of solid carbon dioxide while stirring, is divided between 20 cc of methylene chloride and 7 cc of 2 N ammonia, the aqueous phase is extracted with 10 cc of methylene chloride, the organic phases are washed with water, dried with sodium sulphate and concentrated by evaporation.

The residue is (3S,14S,16S)-9-fluorovincamine with small amounts of (3S,16S)-9-fluoroapovincamine and (3S,14R,16S)-9-fluoro-14-epivincamine as by-products. Crystallization from toluene yields (3S,14S,16S)-9-fluoro-vincamine.

M.P. 210° (dec.); $[\alpha]_D^{20} = +6.0°$ (1%, CHCl$_3$).

| NMR spectrum (CDCl$_3$, 100 megacycles per second): | |
|---|---|
| 0,88 | (T, 7 c.p.s./H$_3$C(21) / 3 H) |
| 1,18–3,50 | (M / 14 H) |
| among them at ap. 2,09 + 2,17 (AB, 13 c.p.s./H$_2$C(15) ) | |
| at 3,23 (H$_2$C(6) ) | |
| 3,79 | (S / H$_3$COOC(22) / 3 H) |
| 3,86 | (S / HC(3) / 1 H) |
| 4,64 | (S / HO—C(14) exchangeable / 1 H) |
| 6,57–7,20 | (M / HC(10 + 11 + 12) / 3 H) |

(3R,14R,16R)-9-fluoro-vincamine, having the same characteristics as (3S,14S,16S)-9-fluoro-vincamine, but an inverse direction of rotation, is obtained in analogous manner, using (3R,16R)-9-fluoro-apovincamine as starting material.

EXAMPLE 8: (3S,14S,16S)-11-chloro-vincamine [process variant a)]

(3S,14S,16S)-11-chloro-vincamine is obtained in a manner analogous to that described in Example 1 by reacting a mixture of the Z and E isomers of 3-[(1S,12bS)-1-ethyl-10-chloro-1,2,3,4,6,7,12,12b-octahydro-indolo[2,3-a]quinolizin-1-yl]-2-methoxypropenoic acid methyl ester with hydrogen bromide in acetic acid.

M.P. 222° (dec.); $[\alpha]_D^{20} = +1.7°$ (0,1%, CHCl$_3$).

| NMR spectrum (CDCl$_3$, 100 megacycles per second): | |
|---|---|
| 0,87 | (T, 7c.p.s./ H$_3$C(21) / 3 H) |
| 1,08–3,46 | (M / 14 H) |
| among them at 2,07 + 2,17 (AB, 14c.p.s./H$_2$C(15) ) | |
| 3,78 | (S / H$_3$COOC(22) ) and |
| 3,82 | (shoulder / HC(3) /together 4 H); |
| 4,55 | (broad / HO—C(14), exchangeable / 1 H) |
| 6,94–7,40 | (M / HC(9 + 10 + 12) / 3 H) |

EXAMPLE 9: (3S,14S,16S)-9-hydroxy-vincamine [process variant a)]

(3S,14S,16S)-9-hydroxy-vincamine is obtained in a manner analogous to that described in Example 1 by reacting a mixture of the Z and E isomers of 3-[(1S,12bS)-1-ethyl-8-hydroxy-1,2,3,4,6,7,12,12b-octahydro-indolo[2,3-a]quinolizin-1-yl]-2-methoxypropenoic acid methyl ester with hydrogen bromide in acetic acid.

M.P. 220° (decomp.) from methylene chloride; $[\alpha]_D^{20} = +13.5°$ (1%, CHCl$_3$).

| NMR spectrum (CD$_3$SOCD$_3$, 100 megacycles per second): | |
|---|---|
| 0,83 | (T, 7 c.p.s. / H$_3$C(21) / 3 H) |
| 1,02–3,40 | (M /14 H) |
| among them at 2,13 + 2,21 (AB, 15 c.p.s. /H$_2$C(15) ) | |
| at 3,10 (S / H$_2$C(6) ) | |
| 3,67 | (S / H$_3$COOC(22) / 3 H) |
| 3,71 | (S / HC(3) / 1 H) |
| 5,69 | (S /½CH$_2$Cl$_2$ / 1 H) |
| 6,34 | (D, 7 c.p.s. / HC(10) / 1 H) |
| 6,50 | (D, 8 c.p.s. / HC(12) / 1 H) |
| 6,60 | (S / HO—C(14), exchangeable / 1 H) |
| 6,73 | (ap. T, 8 + 7 c.p.s./HC(11) / 1 H) |
| 9,06 | (S / HO—C(9), exchangeable / 1 H) |

EXAMPLE 10: (3S,14S,16S)-12-methyl-vincamine [process variant a)]

(3S,14S,16S)-12-methyl-vincamine is obtained in a manner analogous to that described in Example 1 by reacting a mixture of the Z and E isomers of 3-[(1S,12bS)-1-ethyl-11-methyl-1,2,3,4,6,7,12,12b-octahydro-indolo[2,3-a]quinolizin-1-yl]-2-methoxypropenoic acid methyl ester with hydrogen bromide in acetic acid.

M.P. 224° (dec.); $[\alpha]_D^{20} = +7.6°$ (1%, CHCl$_3$).

| NMR spectrum (CDCl$_3$, 90 megacycles per second): | |
|---|---|
| 0,89 | (T, 7c.p.s. / H$_3$C(21) / 3 H) |
| 1,13–3,43 | (M / 17 H) |
| among them at 2,00 + 2,19 (AB,14c.p.s./ H$_2$C(15) ) | |
| at 2,47 (S / CH$_3$C(12) ) | |
| 3,81 | (S / H$_3$COOC(22) / 3 H) |
| 3,86 | (S / HC(3) / 1 H) |
| 3,99 | (S / HO—C(14), exchangeable / 1 H) |
| 6,82–7,44 | (M / HC(9 + 10 + 11) / 3 H) |

EXAMPLE 11: (3S,14S,16S)-10-bromo-vincamine (a) (3S,14S,16S)-vincamine is brominated according to the procedure described in Example 6 [process c)]. (3S,14S,16S)-11-bromovincamine is crystallized out from the isopropyl alcohol solution obtained before chromatographic purification. The mother liquors of this first crystallization (containing 10- and 11-bromovincamine) are boiled for 3 hours in 40 ml of formic acid. The reaction mixture is concentrated. The residue is partitioned between methylene chloride and 5N aqueous ammonia. The organic phase is concentrated. The residue is crystallized several times from methylene chloride/cyclohexane to yield (3S,16S)-10-bromo-vincamine.

(b) (3S,16S)-10-bromo-apovincamine is treated with hydrogen bromide and the resulting product hydrolysed in accordance with the procedure described in Example 5 [process b)]. (3S,16S)-10-bromo-apovincamine and (3S,14R,16S)-10-bromo-epivincamine are obtained as by-products. (3S,14S,16S)-10-bromo-vincamine has M.Pt. 203° (decomp.) and $[\alpha]_D^{20} = 35.2$ (1% $CHCl_3$).

10 Bromo-vincamine may be made as follows:

EXAMPLE 1A: (−)-15-bromovincadifformine (a) Direct Process

A solution of 20 g (−)-vincadifformine base in 200 ml chloroform is saturated with HCl gas at 20°. A solution of 9.92 g bromine in 40 ml chloroform is added dropwise over 25 minutes. After 30 minutes stirring the reaction mixture is poured onto 500 ml ice and 10 g sodium carbonate. The organic phase is separated off, washed and dried. The dried organic phase may be worked up to give (−)-15-bromovincadifformine [hydrogen fumarate M.Pt. 200°-201° $[\alpha]_D^{20} = -445°$ (c = 1 in acetone)].

(b) Alternative Process

A solution of 2.36 g bromine in 20 ml chloroform is added to a solution of 5 g (−)-vincadifformine in 20 ml chloroform maintained at −20° C. The reaction mixture is poured onto ice and sodium bicarbonate. The organic phase is separated off, washed, dried, evaporated at 50° C. and chromatographed to yield an elution with chloroform and 5% acetone 3-bromo-1,2-didehydroaspidospermidine-3-carboxylic acid methyl ester M.Pt. from 95° C. (decomp.).

The methyl ester is immediately treated at 20° C. with hydrogen bromide gas in chloroform to yield after working up (−)-15-bromovincadifformine.

EXAMPLE 2A:
15-bromo-1,2-didehydro-3-hydroxy-aspidosperidine-3-carboxylic acid methyl ester 9-oxide The dried organic phase obtained from Example 1A is treated portionwise at 20° with 20.4 g 82.5% m-chloroperbenzoic acid and allowed to stand for 30 minutes. The mixture is washed with 5% (w/v) sodium carbonate solution, dried over sodium sulphate and concentrated in a vacuum at 50°. The residue is treated with 200 ml acetone to give crystals of the title compound, M.Pt. (from acetone/chloroform) 202°-205° (decomp.).

EXAMPLE 3A: (+)-[(3S, 14S, 16S)]-10-bromovincamine

A solution of 20 g of the 9-oxide obtained from Example 2, 400 ml acetic acid, 40 ml water and 17.4 g triphenylphosphine is stirred for 4 hours at 50°. The reaction mixture is concentrated in a vacuum and the residue treated with sodium hydroxide solution. The base thereby formed is taken up in chloroform and chromatographed on silica-gel eluting (+)-10-bromovincamine base with chloroform containing 3% methanol. M.Pt. 202°-205°; $[\alpha]_D^{20} = +35.2°$ (c = 1 in $CHCl_3$). A more polar fraction yields [(3S, 14R, 16S)]-10-bromo-epivincamine. M.Pt. 195°-196° $[\alpha]_D^{20} = -8.6°$ (c = 1 in $CHCl_3$) which may be converted into (+)-10-bromovincamine in conventional manner.

EXAMPLE 4A: (+)-[(3S, 14S, 16S)]-10-bromovincamine

A solution of 4.17 g (−)-15-bromovincadifformine in 100 ml toluene is treated at 5° with 1.15 g trifluoroacetic acid. The mixture containing a compound of formula II wherein n is 1 and Y is trifluoroacetate is maintained at 5° and 2.00 g para-nitroperbenzoic acid is added portionwise. The mixture is allowed to warm to room temperature, maintained for 15 hours, and then evaporated to dryness. The residue containing a compound of formula I wherein n is 1 and Y is trifluoroacetate is taken up in 45 ml glacial acetic acid and 5 ml water. The mixture is stirred for two hours at room temperature, then adjusted to pH 9 by the addition of sodium hydroxide, and extracted three times with dichloromethane. Washing with water, drying over sodium sulphate, evaporation and resultant chromatography as in Example 3A, yields the title compound and [(3S, 14R, 16S)]-10-bromoepivincamine.

The compounds of formula I are furthermore useful as vigilance-increasing and psychostimulant agents, as indicated by an increase in excitability observed in mice on p.o. administration of from 10 to 100 mg/kg animal body weight of the compounds, and furthermore by a decrease in sleep and increase in wakefulness as observed in the electroncephalogram on i.p. or p.o. administration of from 10 to 30 mg/kg animal body weight of the compounds.

The compounds are therefore useful as agents for the treatment of cerebral insufficiency, and as C.N.S. stimulant agents.

For this use the dosage will, of course, vary depending on the compound employed, mode of administration and treatment desired. However, in general, satisfactory results are obtained when administered at a daily dosage of from about 0.01 mg to about 100 mg per kg animal body weight, conveniently given in divided doses 2 to 4 times a day or in sustained release form. For the larger mammals, the total daily dosage is in the range from about 1 to about 500 mg, and dosage forms suitable for oral administration comprise from about 0.25 mg to about 250 mg of the compounds admixed with a solid or liquid pharmaceutical carrier or diluent.

The (3S,14S,16S) compounds are preferred.

(3S,14S,16S)-10-bromo- and -10-fluoro-vincamine and (3S,14S,16S)-11-bromovincamine are the preferred compounds.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

The 14-epi forms of the compounds of formula I are useful intermediates for the preparation of pharmacologically active compounds, for example, for the preparation of the corresponding apovincamines of formula III by dehydration in conventional manner.

I claim:

1. A compound of formula I,

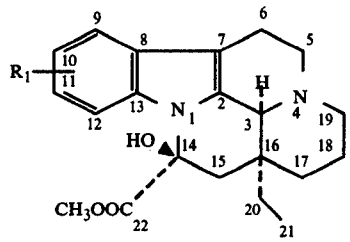

I wherein $R_1$ is bromine, fluorine, chlorine, or lower alkyl, or a pharmaceutically acceptable acid addition salt thereof, in racemic form or in individual optical isomer form.

2. The compound of claim 1 which is 10-fluorovincamine.

3. The compound of claim 1, which is 11-bromovincamine.

4. The compound of claim 1, which is 9-fluorovincamine.

5. The compound of claim 1, which is 11-chlorovincamine.

6. The compound of claim 1, which is 12-methylvincamine.

7. A compound of claim 1 in racemic form.

8. A compound of claim 1 in individual optical isomer form.

9. A compound of claim 8 having the (3S,14S,16S) configuration.

10. A compound of claim 8 having the (3R,14R,16R) configuration.

11. A 14-epi-isomer of a compound of claim 1.

12. A compound of claim 1, wherein $R_1$ is bromine.

13. A compound of claim 1, wherein $R_1$ is fluorine.

14. A compound of claim 1, wherein $R_1$ is chlorine.

15. A compound of claim 1, wherein $R_1$ is lower alkyl.

16. A compound of claim 1, wherein $R_1$ is in the 9-position.

17. A compound of claim 1, wherein $R_1$ is in the 10-position.

18. A compound of claim 1, wherein $R_1$ is in the 11-position.

19. A compound of claim 1, wherein $R_1$ is in the 12-position.

20. A compound of claim 1, wherein $R_1$ is Br in the 10-position.

21. A compound of claim 1, chosen from (3S,14S,16S)-10-fluorovincamine, (3S,14S,16S)-10-bromovincamine, and (3S,14S,16S)-11-bromovincamine.

22. A vigilance increasing pharmaceutical composition comprising an effective vigilance increasing amount of a compound of claim 1 in association with a pharmaceutical carrier or diluent.

23. A method of increasing vigilance in animals, which comprises administering to an animal in need of such treatment a therapeutically effective amount of a compound of claim 1.

24. A method of treating cerebral insufficiency in animals, which comprises administering to an animal in need of such treatment a therapeutically effective amount of a compound of claim 1.

* * * * *